(12) United States Patent
Kobayashi et al.

(10) Patent No.: US 10,660,617 B2
(45) Date of Patent: May 26, 2020

(54) ULTRASONIC PROBE

(71) Applicant: Toshiba Medical Systems Corporation, Otawara-shi (JP)

(72) Inventors: Yusuke Kobayashi, Otawara (JP); Yasuhiro Ona, Nasushiobara (JP); Takashi Takeuchi, Otawara (JP); Tomohiro Sato, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 186 days.

(21) Appl. No.: 15/669,117

(22) Filed: Aug. 4, 2017

(65) Prior Publication Data

US 2018/0042580 A1 Feb. 15, 2018

(30) Foreign Application Priority Data

Aug. 10, 2016 (JP) ................. 2016-157935

(51) Int. Cl.
*A61B 8/00* (2006.01)
*G01S 7/52* (2006.01)
*G01S 15/89* (2006.01)

(52) U.S. Cl.
CPC ............ *A61B 8/546* (2013.01); *A61B 8/4455* (2013.01); *A61B 8/4444* (2013.01); *A61B 8/4494* (2013.01); *G01S 7/5205* (2013.01); *G01S 15/8906* (2013.01); *G01S 15/8927* (2013.01)

(58) Field of Classification Search
CPC ......... A61B 8/44; A61B 8/546; A61B 8/4444; A61B 8/4494
See application file for complete search history.

(56) References Cited

U.S. PATENT DOCUMENTS

| 2014/0058270 A1 | 2/2014 | Davidsen et al. |
| 2017/0135673 A1* | 5/2017 | Bruestle ............... A61B 8/4455 |
| 2017/0156697 A1* | 6/2017 | Cho ........................ A61B 8/00 |

FOREIGN PATENT DOCUMENTS

| JP | 06-121389 | 4/1994 |
| JP | 2014-516686 | 7/2014 |

* cited by examiner

*Primary Examiner* — David M. Gray
*Assistant Examiner* — Andrew V Do
(74) *Attorney, Agent, or Firm* — Oblon, McClelland, Maier & Neustadt, L.L.P.

(57) ABSTRACT

According to one embodiment, an ultrasonic probe includes a plurality of ultrasonic transducers, an electronic circuit, an insulative heat conductive spacer and an electrical heat supporting element. The electronic circuit is electrically connected to a plurality of transducers on one side. The insulative heat conductive spacer contacts with another side of the electronic circuit. The electrical heat supporting element has a contact region that makes contact, in a first surface, with the insulative heat conductive spacer, and a supporting structure that supports the insulative heat conductive spacer to have a predetermined thickness, and diffuses heat generated by the electronic circuit from the contact region.

11 Claims, 9 Drawing Sheets

ULTRASONIC PROBE

CROSS-REFERENCE TO RELATED APPLICATIONS

This application is based upon and claims the benefit of priority from the prior Japanese Patent Application No. 2016-157935, filed Aug. 10, 2016, the entire contents of all of which are incorporated herein by reference.

FIELD

Embodiments described herein relate generally to ultrasonic probes.

BACKGROUND

As an ultrasonic probe utilized in ultrasonic diagnostic apparatuses, there is an array-type ultrasonic probe in which a plurality of ultrasonic transducers are arrayed. Recently, in particular, a two-dimensional array probe makes its market debut, in which a plurality of ultrasonic transducers is two-dimensionally arrayed, allowing three-dimensional scanning for a diagnostic target region of an object.

In an ultrasonic probe having a huge number of ultrasonic transducers (i.e., the number of channels) typified by such a two-dimensional array probe, the number of wiring required for transmission and reception between the ultrasonic probe and the body of the ultrasonic diagnostic apparatus is also apt to be a huge number. This may consequently lead to a large-sized ultrasonic probe and a reduction in cable-operability.

To prevent such a problem, a means is provided so that at least part of electronic circuits for executing ultrasonic transmission and reception is provided, as ASICs (Application Specific Integrated circuits), in an ultrasonic probe, not in an ultrasonic diagnostic apparatus, and after generating a drive signal, or making the number of received signals in a predetermined signal number, in the ultrasonic probe, these signals are then sent to the ultrasonic diagnostic apparatus body. In this case, to miniaturize the ultrasonic probe, there may be a case where the ASIC is provided as a bare chip. (In general, an ASIC is encapsulated in a package, such as plastic, and the package is mounted on the board. The wording "an ASIC as a bare chip" means an ASIC in a state of being free from such a package. By mounting an ASIC as a bare chip on a board, for example, miniaturization by one package can be realized.)

However, if an ASIC is provided in an ultrasonic probe, there is a need to diffuse a quantity of heat generated by the ASIC. If the ASIC provided in the probe is a bare chip, the diffusion of the quantity of heat generated by the ASIC is a further significant technical problem. In order to efficiently diffuse the quantity of heat generated by such an ASIC and a quantity of heat generated by each ultrasonic transducer, conventional ultrasonic probes adopt methods such as using a cooling medium to aggressively cool heat (active cooling method), or a method of diffusing heat by contacting a heat conductive member with the heat source without using a cooling medium (passive cooling method).

DETAILED DESCRIPTION

If an ASIC is provided as a bare chip in an ultrasonic probe, it is necessary to ensure electrical insulation properties between the ASIC and other members or components. However, insulators generally have low thermal conductivity as compared to metals, and thus easy insulation protection impairs the heat suppression of probe heads. Furthermore, it is necessary to ensure the productivity of member precision, in addition to ensuring thermal diffusion and electric insulation properties. These properties cannot be ensured by conventional ultrasonic probes.

In general, according to one embodiment, an ultrasonic probe includes a plurality of ultrasonic transducers, an electronic circuit, an insulative heat conductive spacer and an electrical heat supporting element. The plurality of ultrasonic transducers generate an ultrasonic wave based on a drive signal supplied, and generate an electric signal based on the received ultrasonic wave. The electronic circuit is electrically connected to the plurality of transducers on one side to execute at least one of control relating to the drive signal, and processing relating to the electric signal. The insulative heat conductive spacer contacts with another side of the electronic circuit. The electrical heat supporting element has a contact region that makes contact, in a first surface, with the insulative heat conductive spacer, and a supporting structure that supports the insulative heat conductive spacer to have a predetermined thickness, and diffuses heat generated by the electronic circuit from the contact region.

Hereinafter, the present embodiment will be explained in accordance with the drawings. Note that in the following explanations, structural elements having almost the same function and structure are provided with the same symbols, and an overlapped explanation is provided only when needed.

To specifically explain the present embodiment, the present embodiment will be explained using an example of a two-dimensional array probe in which a plurality of ultrasonic transducers is arrayed in a matrix form. However, the configuration for the thermal diffusion and the electrical insulation in the probe according to the present embodiment is not limited to the example of the two-dimensional array probe, and thus a one-dimensional array probe, and a 1.5-dimensional array probe are also applicable.

Figure 1:
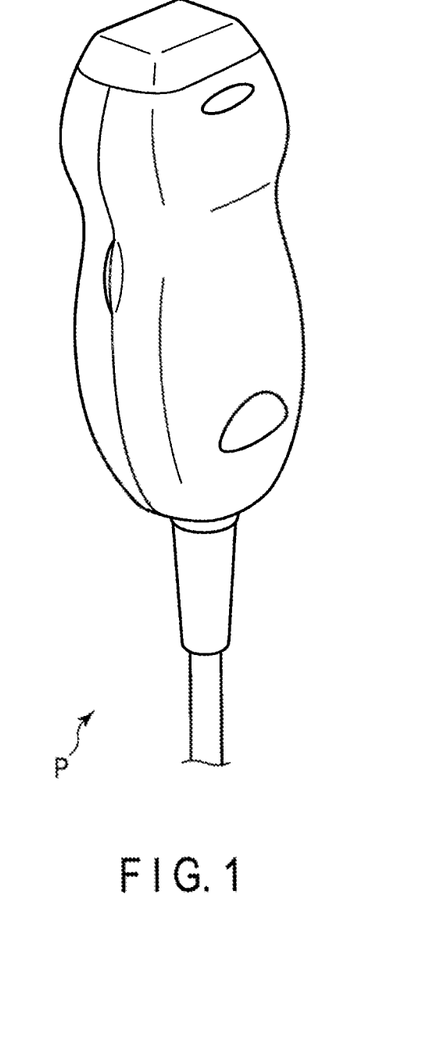
FIG. 1 is an external view of an ultrasonic probe P according to the present embodiment.
Figure 2:
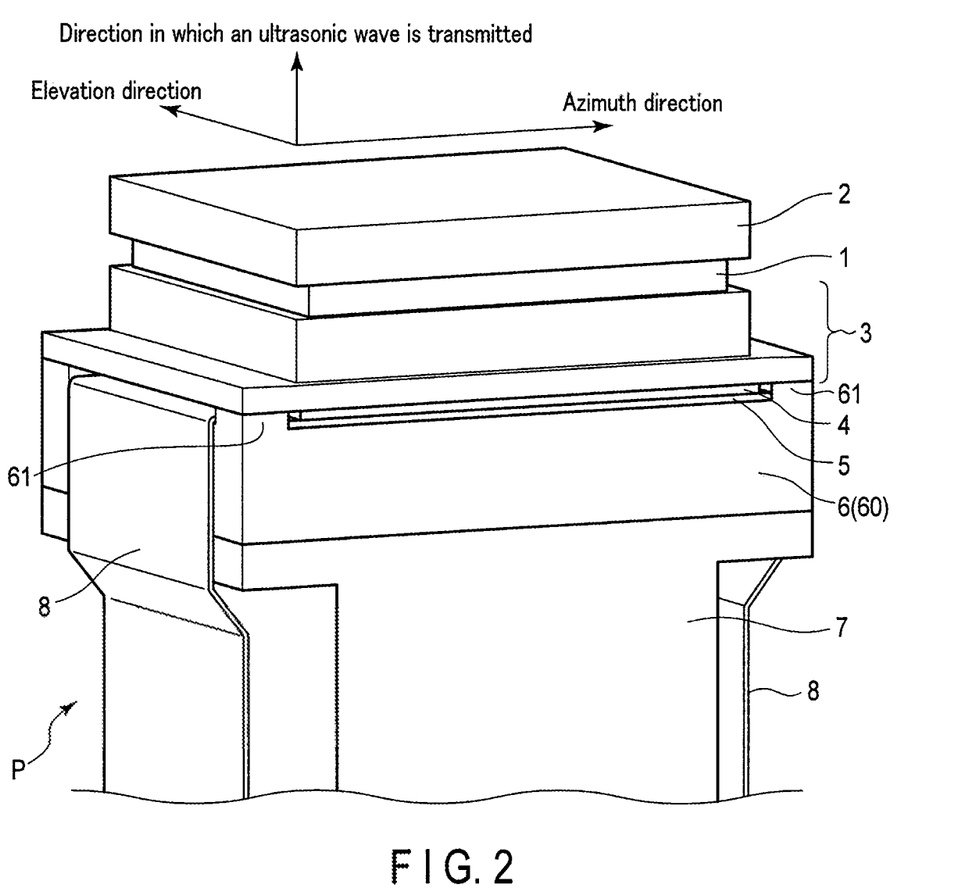
FIG. 2 is a perspective view showing an internal structure of the ultrasonic probe P shown in FIG. 1.
Figure 3:
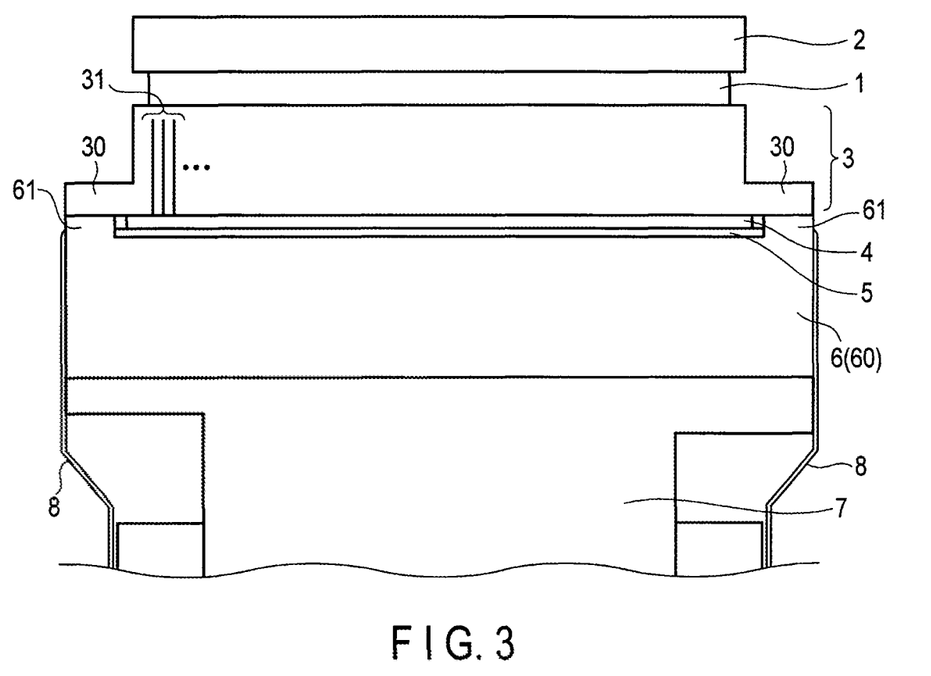
FIG. 3 is a side view when viewing the ultrasonic probe P shown in FIG. 2 along an elevation direction.
Figure 4:
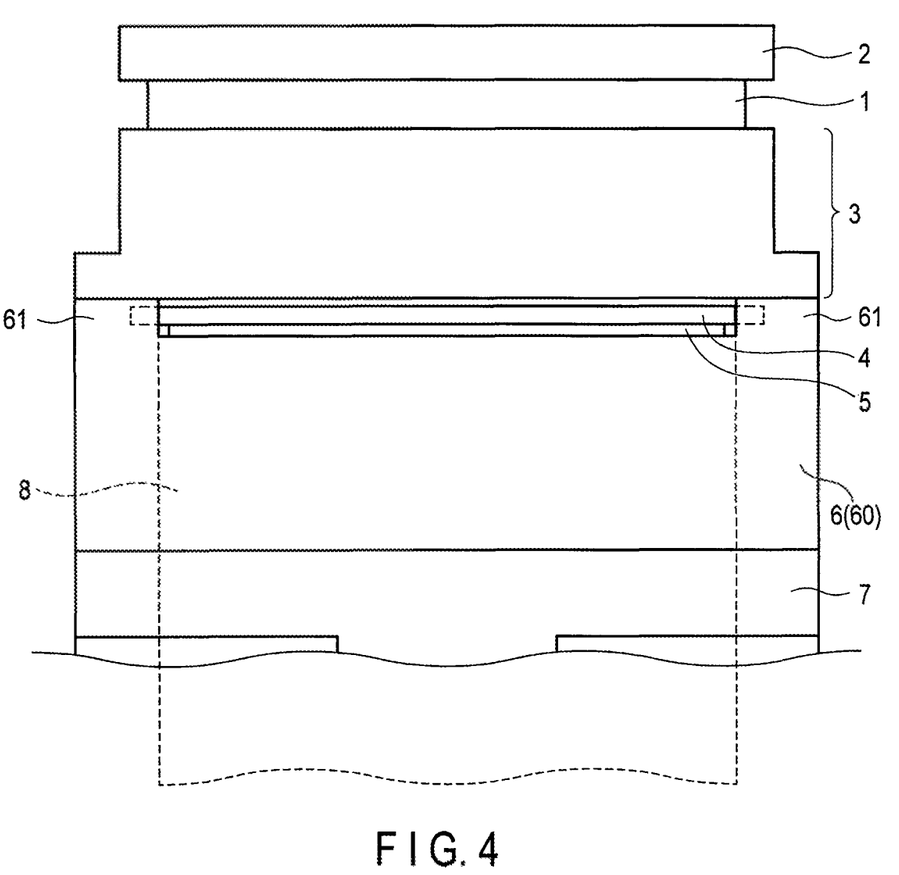
FIG. 4 is a side view when viewing the ultrasonic probe P shown in FIG. 2 along an azimuth direction.

FIG. 1 is an external view of an ultrasonic probe P according to the present embodiment. FIG. 2 is a perspective view showing an internal structure of the ultrasonic probe P shown in FIG. 1. FIG. 3 is a side view in a case of viewing the ultrasonic probe P shown in FIG. 2 along an elevation direction. FIG. 4 is a side view in a case of viewing the ultrasonic probe P shown in FIG. 2 along an azimuth direction.

The ultrasonic probe P includes a transducer layer 1, an acoustic matching layer 2, an IP board 3, a plurality of ASICs 4, an insulative heat conductive spacer 5, an electrical heat supporting element 6, a supporting member 7, and a flexible printed circuit board (FPC board) 8. Note that the electrical heat supporting element 6, the supporting member 7, and the like constitute a main frame of the ultrasonic prove P.

The transducer layer 1 includes a plurality of ultrasonic transducers which are arrayed in an azimuth direction and in an elevation direction. The ultrasonic transducers include piezoelectric elements and electrodes, transmit an ultrasonic wave in a desired direction within a scanned region based on the drive signal, for example, from ASICs 4 and convert a reflected wave from the object into an electric signal. Note that on the opposite side of the transducer layer 1 in a direction to which the ultrasonic wave is transmitted, a backing member is provided, although it is unillustrated. The plurality of ultrasonic transducers of the transducer layer 1 are classified into a plurality of groups (sub-arrays), and execute control associated with transmission of the ultrasonic wave, control associated with reception of the ultrasonic wave, and the signal processing, based on the sub-arrays.

The acoustic matching layer 2 is provided on the transducer layer 1 on the side of the direction to which the ultrasonic wave is transmitted, and efficiently propagates an ultrasonic wave energy between the ultrasonic transducers and a living body. Note that the number of the acoustic matching layers 2 is not limited to one layer, and a plurality of the acoustic matching layers 2 may be formed.

The IP board 3 has a function to relay an electrical connection between each ultrasonic transducer and the ASICs 4 in the transducer layer 1, and includes a board having a certain degree of rigidity, such as a glass-epoxy multilayer board, and ceramic multilayer board. The IP board 3 includes, on its surface on the side of the direction to which the ultrasonic wave is transmitted, a plurality of unillustrated first electrode pads which are provided so as to correspond to the signal electrode of each of the ultrasonic transducers. The signal electrode of each of the ultrasonic transducers is electrically connected to the first electrode pad on the top surface, by using a means of ACF adhesion, a conductive adhesive, or an Au bump. Furthermore, the IP board 3 includes, on the opposite surface (back surface) of the surface on the side of the direction to which the ultrasonic wave is transmitted, a plurality of unillustrated second electrode pads which are electrically connected to the electrode of ASICs3 by using a means of an Au bump, and a plurality of wiring 31 that electrically connect the first electrode pads and the second electrode pads (The wiring 31 that electrically connects the first electrode pads to the second electrode pads is not present in a projection 30.). This IP board 3 enables each of the ultrasonic transducers to be connected, as an independent channel, to a corresponding ASIC 4, even if the electrode pitch of the ASICs3 differs from the electrode pitch of the plurality of ultrasonic transducers arrayed in the transducer layer 1.

ASIC 4 are integrated circuits, and a plurality of ASICs 4 are mounted on the back surface of the IP board 3 at predetermined intervals. Each of the ASICs 4 are correlated with a sub-array of the ultrasonic transducers and executes control associated with transmission of the plurality of ultrasonic transducers constituting each sub-array (e.g., control associated with a drive signal) and control and processing associated with reception (e.g., amplification and delayed addition of an electric signal based on a reflected wave).

The insulative heat conductive spacer 5 is a spacer having high electrical insulation properties (voltage resistance), high thermal conductivity, high elasticity and plasticity, and manufactured using, for example, a silicon material. The insulative heat conductive spacer 5 electrically insulates ASICs 4 from the other components and members and diffuses heat generated in ASICs 4 in the opposite direction (rear surface direction or back surface direction) of the direction to which the ultrasonic wave is transmitted.

The electrical heat supporting element 6 is laminated on a structure comprising the acoustic matching layer 2, transducer layer 1, and IP board 3 to support the structure and further diffuses, in the back surface direction, heat that has been diffused via the insulative heat conductive spacer 5. The electrical heat supporting element 6 has a supporting structure for maintaining the insulative heat conductive spacer 5 to have a predetermined thickness and a predetermined form. This supporting structure will be explained in detail later.

The supporting member 7 supports the electrical heat supporting element 6 and further diffuses, in the back surface direction, heat that has been diffused via the electrical heat supporting element 6.

The flexible print board (FPC board) 8 includes a predetermined wiring pattern for transmitting and receiving an electric signal between the ultrasonic probe P and an ultrasonic diagnostic apparatus body to which the ultrasonic probe P is connected; each electrode for the plurality of ultrasonic transducers, and a plurality of electrodes which are electrically connected to each of the electrodes of ASICs 4. The FPC board 8 is drawn from between poles 61 on the top surface of the electrical heat supporting element 6, and is guided to the cable side.

(Supporting Structure for Maintaining the Insulative Heat Conductive Spacer to have a Predetermined Thickness)

A supporting structure for maintaining an insulative heat conductive spacer provided to the ultrasonic prove P of the present embodiment to have a predetermined thickness will be explained.

Figure 5:
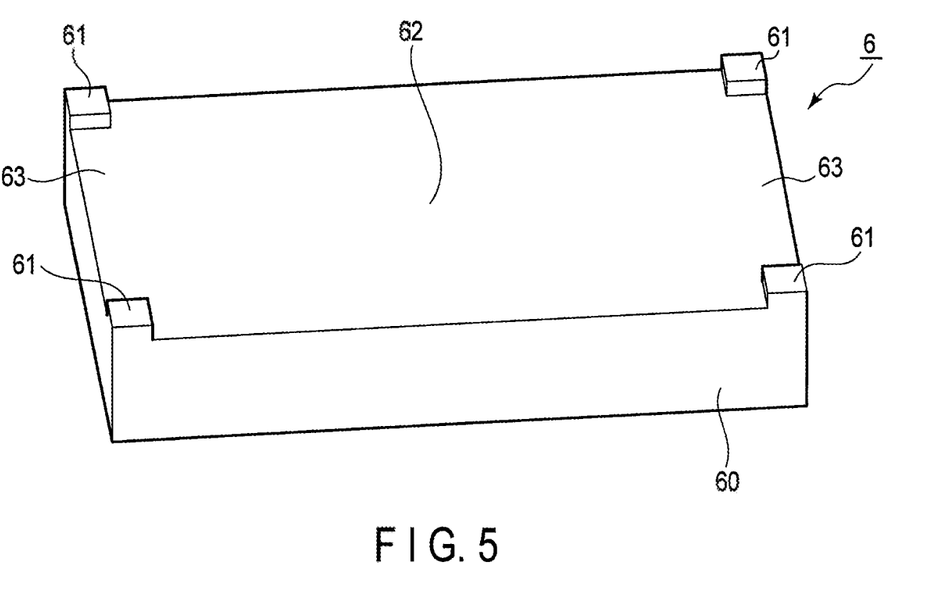
FIG. 5 is an enlarged perspective view of the electrical heat supporting element 6 shown in FIGS. 2, 3 and 4.

FIG. 5 is an enlarged perspective view of the electrical heat supporting element 6 shown in FIGS. 2, 3, and 4. As shown in FIG. 5, the electrical heat supporting element 6 includes an electrical heat supporting element body 60 and poles 61.

The electrical heat supporting element body 60 has, for example, a generally rectangular parallelepiped shape, and is formed with a material having high thermal conductivity and high rigidity, such aluminum.

The poles 61 are provided, for example, in four corners of a rectangular top surface of the electrical heat supporting element body 60 (a surface of the electrical heat supporting element 6 on the side of the direction to which the ultrasonic wave is transmitted illustrated in FIGS. 2, 3, and 4), and have a predetermined height. In the present embodiment, an electrical heat supporting element 6 is illustrated by way of example, in which the poles 61 and the electrical heat supporting element body 60 are integrally formed as shown in FIG. 5. However, the electrical heat supporting element 6 is not limited thereto and may be structured in such a manner that the poles 61 are separately formed from the electrical heat supporting element body 60, and the poles 61 are fixed on the electrical heat supporting element body 60. In this case, the material of the poles 61 preferably has high thermal conductivity and high rigidity as with the electrical heat supporting element body 60.

Note that between the poles 61 and ASICs 4, an air gap (air layer) as an insulation layer or an insulation layer corresponding to the air layer exists. For this reason, the insulation properties between the poles 61 and ASICs 4 are ensured. However, to achieve higher insulation properties, the poles 61 may be formed to be insulators.

A space surrounded by the four poles 61 on the top surface of the electrical heat supporting element body 60 forms an ASIC/spacer arrangement region 62. On the ASIC/spacer arrangement region 62, the ASICs 4 and the insulative heat conductive spacer 5 that have been laminated on the back surface of the IP board 3 are arranged through an assembling step explained below.

A space lies between the poles 61 on the short side of the top surface of the electrical heat supporting element body 60 forms a FPC board drawing region 63. The flexible printed circuit board (FPC board) 8 is drawn from the FPC board drawing region 63 in the back surface direction of the ultrasonic probe P through an assembling step explained below.

By each of the poles 61 being kept to have a predetermined height, the ASICs 4 and the electrical heat supporting element body 60 placed in the ASIC/spacer arrangement region 62 are arranged to always be a constant distance from each other, and both of them are electrically insulated. Similarly, by each of the poles 61 being kept to have a predetermined height, the insulative heat conductive spacer 5 placed in the ASIC/spacer arrangement region 62 always has a maximum surface area contact with the top surface of the electrical heat supporting element body 60, in a state where the insulative heat conductive spacer 5 is maintained to have a predetermined thickness, to convey heat from the ASICs 4 to the electrical heat supporting element body 60. To ensure such a function, the height of each of the poles 61 is determined in accordance with the thickness of the ASICs 4, the thickness of the insulative heat conductive spacer 5 to ensure sufficient insulation properties, the thickness (thinness) of the insulative heat conductive spacer 5 by which the thermal conductivity can be ensured, and the elastic modulus of the insulative heat conductive spacer 5.

(Assembling Step of Ultrasonic Probe P)

The assembling process of the ultrasonic probe P will be explained in reference to FIGS. 6, 7, 8, and 9.

Figure 6:
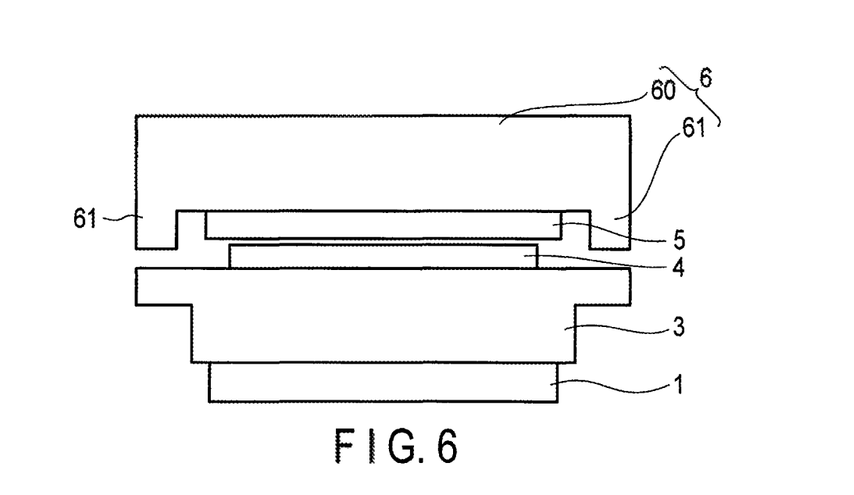
FIG. 6 is a view for illustrating an assembling step of an ultrasonic probe P.
Figure 7:
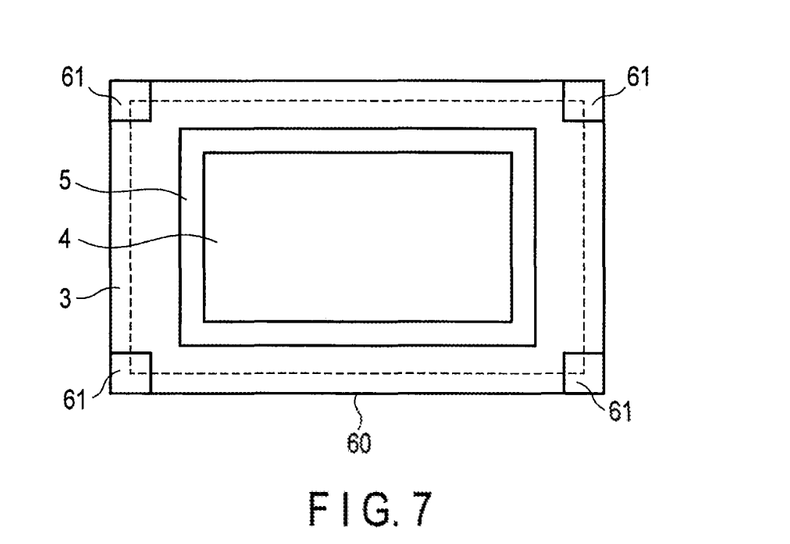
FIG. 7 is a view for illustrating the assembling step of an ultrasonic probe P.

FIGS. 6 and 7 are respectively a side view and a top view before the ASIC/spacer arrangement region 62 in each electrical heat supporting element 6 is pressed against the insulative heat conductive spacer 5 to apply a pressure to the insulative heat conductive spacer 5 (i.e., before the insulative heat conductive spacer 5 is deformed). As shown in FIG. 6, at the stage before pressing the ASIC/spacer arrangement region 62 in the electrical heat supporting element 6 against the insulative heat conductive spacer 5 to apply a pressure thereto, the sum of the thickness (height) of the ASICs 4 laminated on the surface of the IP board 3 opposite to the surface in the direction toward which the ultrasonic wave is transmitted, and of the thickness (height) of the insulative heat conductive spacer 5, is greater than the height of the poles 61 (i.e., the thickness of ASICs 4+the thickness of insulative heat conductive spacer 5>the height of pole 61). As shown in FIG. 7, at the stage before pressing the ASIC/spacer arrangement region 62 in the electrical heat supporting element 6 against the insulative heat conductive spacer 5 to apply a pressure thereto, the area of the insulative heat conductive spacer 5 is slightly greater than the arrangement area of the ASICs 4.

Figure 8:
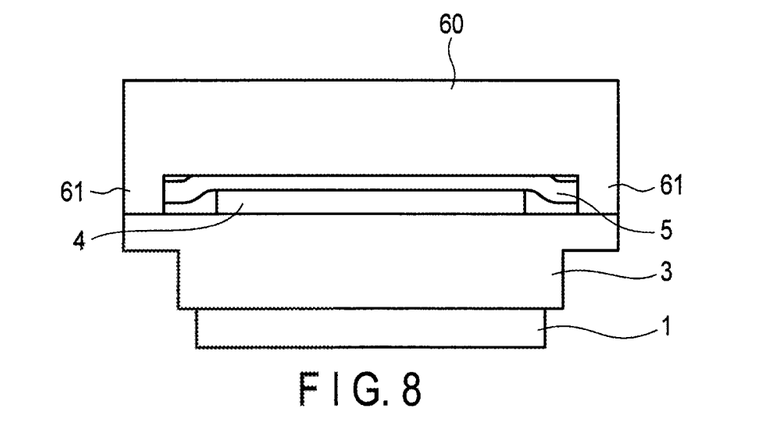
FIG. 8 is a view for illustrating the assembling step of an ultrasonic probe P.
Figure 9:
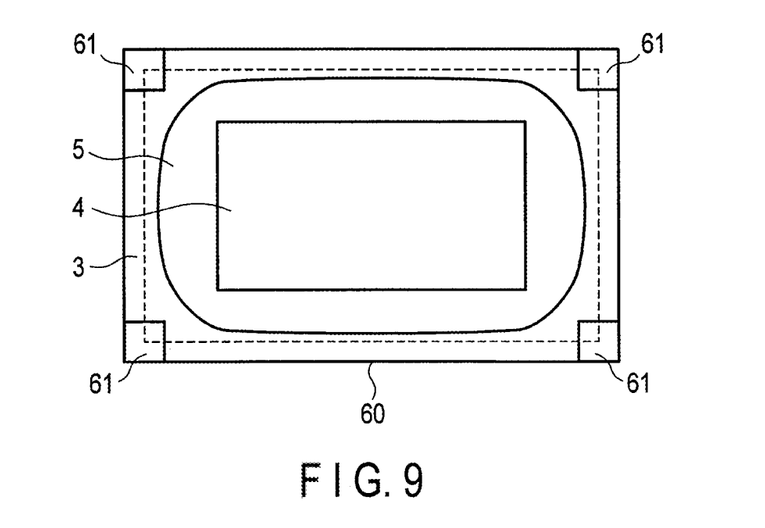
FIG. 9 is a view for illustrating the assembling step of an ultrasonic probe P.

FIGS. 8 and 9 are respectively a side view and a top view after the ASIC/spacer arrangement region 62 in each electrical heat supporting element 6 has been pressed against the insulative heat conductive spacer 5, and a pressure has been applied thereto (i.e., after the insulative heat conductive spacer 5 has been deformed). As shown in FIG. 8, when a certain pressure is applied to the insulative heat conductive spacer 5, the insulative heat conductive spacer 5 is deformed by its elasticity, until the poles 61 in four corners contact the back surface of the IP board 3 (the insulative heat conductive spacer 5 is crushed to escape in a direction where the surface is widened). As a result, as shown in FIGS. 8 and 9, the insulative heat conductive spacer 5 adheres tightly to the ASIC/spacer arrangement region 62, while ensuring a contact area wider than before the pressure is applied. (At this time, the sum of the thickness of the ASICs 4 and the thickness of the insulative heat conductive spacer 5 is substantially equal to the height of the poles 61.) The height of the poles 61 is adjusted so that the insulative heat conductive spacer 5 can maintain insulation properties (From the thermal viewpoint, the insulative heat conductive spacer 5 is preferably made as thin as possible. Therefore, the insulative heat conductive spacer 5 can excellently diffuse heat within the ultrasonic probe P toward the back surface of the ultrasonic probe P, while maintaining the insulation properties.

After the poles 61 in the four corners are brought into contact with the back surface of the IP board 3, the structures of the transducer layer 1, IP board 3, ASICs 4, insulative heat conductive spacer 5, and electrical heat supporting element 6 shown in FIG. 8 are mold-fixed. An unillustrated heat-diffusing part (heat spreader) to further induce heat to the handle case and/or cable is mounted on the back surface of the electrical heat supporting element 6. Furthermore, the FPC board 8 is drawn from the FPC board drawing region 63 located between the poles 61 of both the short sides of the top surface of the electrical heat supporting element body 60, and is induced to the cable on the back surface side of the electrical heat supporting element body 60 (Refer to FIG. 4). In this way, heat from the heat generating source can be diffused and distributed evenly by the thermally connected electrical heat supporting element 6, while insulatively protecting the ASICs 4 from other parts/members.

Modification Example 1

Figure 10:
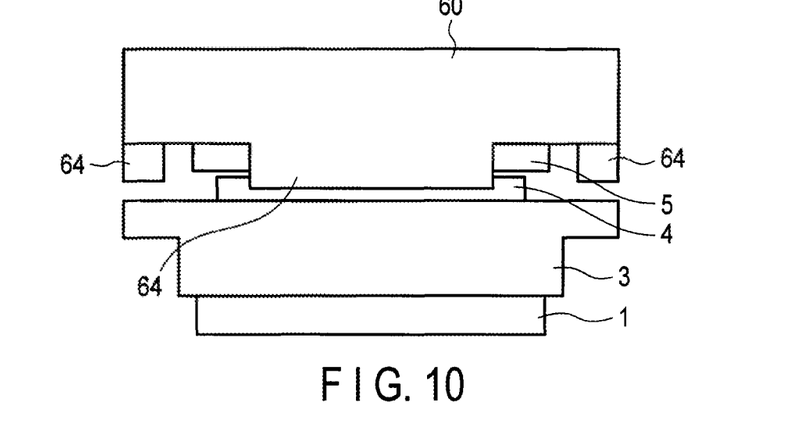
FIG. 10 is a view for illustrating a Modification Example 1 of the probe P according to the present embodiment.
Figure 11:
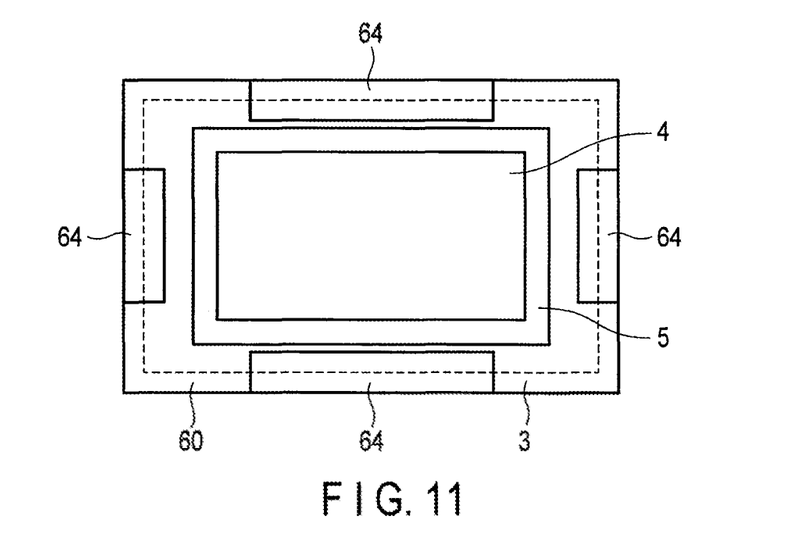
FIG. 11 is a view for illustrating the modification example 1 of the probe P according to the present embodiment.

FIGS. 10 and 11 are views for illustrating Modification Example 1 of the ultrasonic probe P of the present embodiment. FIGS. 10 and 11 respectively illustrate a side view and a top view for the structures of an ultrasonic transducer 1, an IP board 3, ASICs 4, an insulative heat conductive spacer 5, and an electrical heat supporting element 6.

As shown in FIGS. 10 and 11, the electrical heat supporting element 6 of the ultrasonic probe P illustrated in the present Modification Example 1 includes a wall 64 at each long side and each short side of the top surface in the direction where the ultrasonic wave is transmitted. This structure can be adopted, for example, in a configuration where the FPC board is not drawn from the short side and/or long side of the electrical heat supporting element body 60. Also, by the supporting structure according to the Modification Example 1, heat from the heat generating source can be diffused and distributed evenly by means of the thermally connected electrical heat supporting element 6, while insulatively protecting the ASICs 4 from other parts/members.

Modification Example 2

Figure 12:
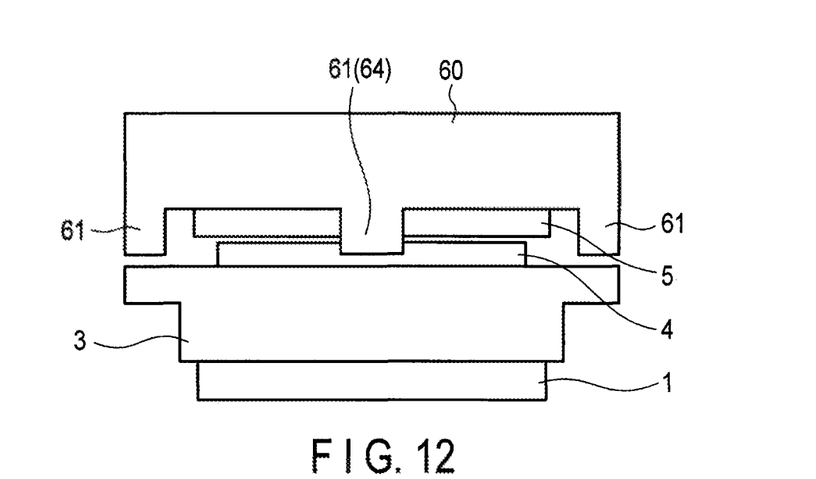
FIG. 12 is a view for illustrating a modification example 2 of the probe P according to the present embodiment.
Figure 13:
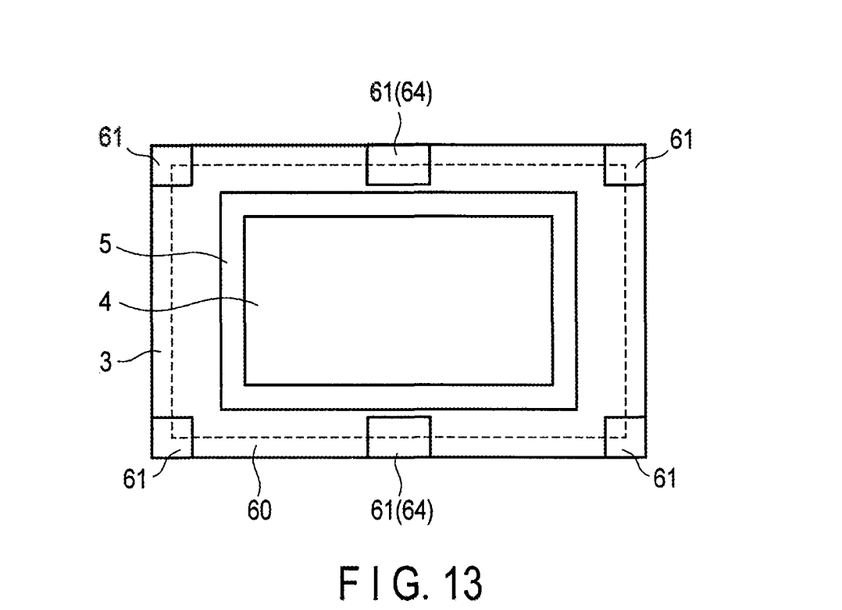
FIG. 13 is a view for illustrating a modification example 2 of the probe P according to the present embodiment.

FIGS. 12 and 13 are views for illustrating Modification Example 2 of the ultrasonic probe P of the present embodiment. FIGS. 12 and 13 respectively illustrate a side view and a top view for the structures of a transducer layer 1, an IP board 3, ASICs 4, an insulative heat conductive spacer 5, and an electrical heat supporting element 6.

As shown in FIGS. 12 and 13, the electrical heat supporting element 6 of the ultrasonic probe P illustrated in the Modification Example 2 includes, in each long side, each short side, and each of the four corners, a pole 61 or wall 64. This structure can be adopted, for example, in a case where the FPC board 8 is drawn from the short sides of the electrical heat supporting element body 60, and where a strength is desired that is higher than in the structure shown in FIG. 5. Also by the supporting structure according to the Modification Example 2, heat from the heat generating source can be diffused and distributed evenly by means of the thermally connected electrical heat supporting element 6, while insulatively protecting the ASICs 4 from other parts/members.

Modification Example 3

The embodiments and each modification example described above show, as examples, some types of electrical heat supporting element 6. However, the position and shape of the supporting structure of the electrical heat supporting element 6 can be modified variously, without limiting to each of the examples described above. For example, the number of poles and the number of walls are not limited, as long as the insulation from the ASICs 4 is ensured. From the viewpoint of the strength, the positions of the IP board 3 and the electrical heat supporting element 6 can be stabilized by providing the poles or walls at at least three points of the top surface of the electrical heat supporting element 6. Each of the examples described above illustrates, as an example, a structure where the poles or walls are provided in peripheral portions of the top surface of the electrical heat supporting element 6, such as each long side, each short side, or four corners of the top surface in the direction where an ultrasonic wave is transmitted. However, the supporting structure of the electrical heat supporting element 6 is not limited to the examples. The poles or walls may be provided, for example, at the center portion of the top surface of the electrical heat supporting element 6 or between ASICs 4 arranged in the ASIC/spacer arrangement region 62 by providing wiring in the IP board 3 so as to widen the space between each of the ASICs 4, while ensuring the insulation of the electrical heat supporting element 6 from the ASICs 4, for example, by the insulative heat conductive spacer 5, or an air layer, or an insulating layer corresponding thereto.

Modification Example 4

The above-mentioned examples and Modification Examples 1 and 3 illustrate a case where the FPC board 8 between the poles 61 of the short sides of the electrical heat supporting element 6 is regarded as a FPC board drawing region. However, the configuration of the present embodiment is not limited thereto. For example, the space between the poles 61 of both of the long sides of the top surface of the electrical heat supporting element body 60 may be formed as a FPC board drawing region, and the FPC board 8 may be drawn from this region.

Modification Example 5

The embodiments and each of the Modification Examples described above are explained, as an example, an ultrasonic probe P in which ASICs 4 are mounted as a bare chip. However, the present embodiment is not limited to the example, and is also applicable to an ultrasonic probe where a packaged ASIC is mounted as needed.

According to the ultrasonic probe of the present embodiment, the insulative heat conductive spacer can always maintain a constant thickness by the supporting structure and the elasticity of itself (i.e., a thickness by which the insulation properties and the thermal conductivity can be ensured), while being contacted with the ASICs and the electrical heat supporting element body. Therefore, the insulative heat conductive spacer can efficiently convey heat generated by the ASICs to the electrical heat supporting element body, and diffuse the heat toward the back surface side of the ultrasonic probe, while electrically insulating the ASICs from the other parts and members. That is, according to the ultrasonic probe in accordance with the present embodiment, the heat inside the probe can be efficiently diffused.

Furthermore, in the assembling step where the ASICs, insulative heat conductive spacer, and the electrical heat supporting element are laminated, by only bringing the insulative heat conductive spacer laminated on the ASICs into contact with the ASIC/spacer arrangement region of the electrical heat supporting element body and applying a pressure in its laminated direction, the insulative heat conductive spacer can be always formed in a constant thickness, while contacting the spacer with the ASICs and the electrical heat supporting element body, by the height of the structure of the poles provided in the vicinity of the ASIC/spacer arrangement region.

Therefore, an ultrasonic probe having electrical insulation properties between ASICs and the main frame, and having thermal conductivity from the ASICs, etc. to the main frame can be manufactured without requesting high member precision. These effects have significant practical benefits, for example, in an ultrasonic probe where ASICs are mounted, as a bare chip, inside the ultrasonic probe.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An ultrasonic probe comprising:
    a plurality of ultrasonic transducers which generate an ultrasonic wave based on a drive signal supplied, and generate an electric signal based on the received ultrasonic wave;

an electronic circuit which is electrically connected to the plurality of transducers on one side to execute at least one of control relating to the drive signal, and processing relating to the electric signal;

an insulative heat conductive spacer which contacts with another side of the electronic circuit; and an electrical heat supporting element which has a contact region that makes contact, in a first surface, with the insulative heat conductive spacer, and a supporting structure that supports the insulative heat conductive spacer to have a predetermined thickness, and which diffuses heat generated by the electronic circuit from the contact region, wherein the electronic circuit is mounted by a bare chip implementation.

2. The probe according to claim 1, wherein the plurality of ultrasonic transducers are arrayed in a two-dimensional matrix form.

3. The probe according to claim 2, wherein the plurality of ultrasonic transducers are classified into a plurality of groups, and the electronic circuit executes at least one of control relating to the drive signal for the ultrasonic transducers included in a corresponding group of the plurality of groups, and control associated with the electric signal.

4. The probe according to claim 1, wherein the supporting structure comprises at least one of (a) poles and (b) walls at at least three portions on the first surface.

5. The probe according to claim 1, wherein the first surface has a rectangular shape, and the supporting structure comprises poles provided at four corners of the first surface.

6. The probe according to claim 5, further comprising a flexible print board that is connected to the electronic circuit and is drawn between the poles provided at the four corners.

7. The probe according to claim 1, wherein the first surface has a rectangular shape, and the supporting structure comprises walls provided on four sides of the first surface.

8. The probe according to claim 1, wherein in a first state before the plurality of ultrasonic transducers, a plurality of electronic circuits and the insulative heat conductive spacer, and the electrical heat supporting element are laminated, a sum of a height of the plurality of electronic circuits in a laminated direction and a height of the insulative heat conductive spacer in the laminated direction is greater than a height of the supporting structure in the laminated direction; and in a second state after the electrical heat supporting element has been laminated, the sum is substantially the same as the height of the supporting structure in the laminated direction.

9. An ultrasonic probe comprising:

a plurality of ultrasonic transducers which generate an ultrasonic wave based on a drive signal supplied, and generate an electric signal based on the received ultrasonic wave;

an electronic circuit which is electrically connected to the plurality of transducers on one side to execute at least one of control relating to the drive signal, and processing relating to the electric signal;

an insulative heat conductive spacer which contacts with another side of the electronic circuit; and an electrical heat supporting element which has a contact region that makes contact, in a first surface, with the insulative heat conductive spacer, and a supporting structure that supports the insulative heat conductive spacer to have a predetermined thickness, and which diffuses heat generated by the electronic circuit from the contact region, wherein the supporting structure comprises at least one of (a) poles and (b) walls at at least three portions on the first surface.

10. The ultrasonic probe as claimed in claim 9, wherein the first surface has a rectangular shape, and the supporting structure comprises walls provided on four sides of the first surface.

11. The ultrasonic probe according to claim 9, wherein the first surface has a rectangular shape, and the supporting structure comprises poles provided at four corners of the first surface, the ultrasonic probe further comprising a flexible print board that is connected to the electronic circuit and is drawn between the poles provided at the four corners.

* * * * *